(12) United States Patent
Francoeur et al.

(10) Patent No.: US 7,942,858 B2
(45) Date of Patent: May 17, 2011

(54) SANITARY NAPKIN INCLUDING BODY-FACING PROTRUSIONS AND ARCUATELY ARRANGED EMBOSSED CHANNELS

(75) Inventors: Julie Francoeur, Montreal (CA); Francisco Javier Valdivia Hernandez, São Jose dos Campos (BR); Yi Zhang, Shanghai (CN)

(73) Assignee: McNeil-PPC, Inc., Skillman, NJ (US)

( * ) Notice: Subject to any disclaimer, the term of this patent is extended or adjusted under 35 U.S.C. 154(b) by 922 days.

(21) Appl. No.: 11/772,926

(22) Filed: Jul. 3, 2007

(65) Prior Publication Data
US 2009/0012489 A1    Jan. 8, 2009

(51) Int. Cl.
*A61F 13/15*    (2006.01)
*A61F 13/20*    (2006.01)

(52) U.S. Cl. .............................................. 604/385.101
(58) Field of Classification Search ............ 604/385.101
See application file for complete search history.

(56) References Cited

U.S. PATENT DOCUMENTS

| | | |
|---|---|---|
| 2002/0193766 A1* | 12/2002 | Gell et al. ................ 604/385.03 |
| 2003/0100874 A1* | 5/2003 | DeCarvalho et al. ......... 604/380 |
| 2004/0254554 A1* | 12/2004 | Mavinkurve et al. ......... 604/380 |

* cited by examiner

*Primary Examiner* — Melanie J Hand

(57) ABSTRACT

A sanitary napkin including a first embossing pattern including a first and second plurality of arcuate channels and a second embossing pattern including a third and fourth plurality of arcuate channels, the channels cooperating to define a plurality of protrusions extending upwardly from the channels.

4 Claims, 4 Drawing Sheets

SANITARY NAPKIN INCLUDING BODY-FACING PROTRUSIONS AND ARCUATELY ARRANGED EMBOSSED CHANNELS

FIELD OF INVENTION

The present invention generally relates to absorbent sanitary napkins and in particular to a sanitary napkin that provides enhanced longitudinal wicking characteristics.

BACKGROUND OF THE INVENTION

In order for a sanitary napkin to efficiently absorb a large amount of fluid during use it must effectively wick fluid throughout the absorbent structure of the napkin. Absent effective wicking properties menstrual fluid tends to pool in certain regions of the napkin as a result of which the full absorbent capacity of the napkin is not effectively utilized.

The present invention relates to an absorbent article having an embossing pattern that provides enhanced wicking characteristics in the longitudinal direction of the absorbent article.

SUMMARY OF THE INVENTION

In view of the foregoing, the present invention provides according to a first aspect of the invention, a sanitary napkin including a cover layer, a barrier layer, an absorbent core arranged between the cover layer and the barrier layer, the absorbent core including first and second longitudinally extending edges and first and second transversely extending edges, a longitudinally extending centerline, a transversely extending centerline, a first and second longitudinal edge, a first and second transverse edge, a first end region and a second end region, a central region arranged between the first and second end regions, a first embossing pattern extending from the first end region towards the center region, the first embossing pattern including a first plurality of arcuate channels and a second plurality of arcuate channels, each one of the channels having a distal end point and a proximal end point, each one of the first plurality of arcuate channels shaped such that the channel arcs in a clockwise direction from its distal end point to its proximal end point, and each one of the second plurality of channels shaped such that the channel arcs in a counter-clockwise direction from its distal end point to its proximal end point, each one of the channels of the first plurality of channels being arranged such that it intersects a plurality of channels of the second plurality of channels and each one of the channels of the second plurality of channels being arranged such that it intersects a plurality of channels of the first plurality of channels, the first plurality of channels being arranged such that adjacent channels of the first plurality of channels cooperate with a plurality of channels of the second plurality of channels to define a plurality of protrusions extending upwardly from the channels, the second plurality of channels being arranged such that adjacent channels of the second plurality of channels cooperate with a plurality of channels of the first plurality of channels to define a plurality of protrusions extending upwardly from the channels, a second embossing pattern extending from the second end region towards the center region, the second embossing pattern including a third plurality of arcuate channels and a fourth plurality of arcuate channels, each one of the channels having a distal end point and a proximal end point, each one of the third plurality of arcuate channels shaped such that the channel arcs in a clockwise direction from its distal end point to its proximal end point, and each one of the fourth plurality of channels shaped such that the channel arcs in a counter-clockwise direction from its distal end point to its proximal end point, each one of the channels of the third plurality of channels being arranged such that it intersects a plurality of channels of the fourth plurality of channels and each one of the channels of the fourth plurality of channels being arranged such that it intersects a plurality of channels of the third plurality of channels, the third plurality of channels being arranged such that adjacent channels of the third plurality of channels cooperate with a plurality of channels of the fourth plurality of channels to define a plurality of protrusions extending upwardly from the channels, the fourth plurality of channels being arranged such that adjacent channels of the fourth plurality of channels cooperate with a plurality of channels of the third plurality of channels to define a plurality of protrusions extending upwardly from the channels.

The present invention provides according to a second aspect of the invention, a sanitary napkin including a cover layer, a barrier layer, an absorbent core arranged between the cover layer and the barrier layer, the absorbent core including first and second longitudinally extending edges and first and second transversely extending edges, a longitudinally extending centerline, a transversely extending centerline, a first and second longitudinal edge, a first and second transverse edge, a first end region and a second end region, a central region arranged between the first and second end regions, a first embossing pattern extending from the first end region towards the center region, the first embossing pattern including a first plurality of arcuate channels and a second plurality of arcuate channels, each one of the channels having a distal end point and a proximal end point, each one of the first plurality of arcuate channels shaped such that the channel arcs in a clockwise direction from its distal end point to its proximal end point, and each one of the second plurality of channels shaped such that the channel arcs in a counter-clockwise direction from its distal end point to its proximal end point, each one of the channels of the first plurality of channels being arranged such that it intersects a plurality of channels of the second plurality of channels and each one of the channels of the second plurality of channels being arranged such that it intersects a plurality of channels of the first plurality of channels, the first plurality of channels being arranged such that adjacent channels of the first plurality of channels cooperate with a plurality of channels of the second plurality of channels to define a plurality of protrusions extending upwardly from the channels, a spacing between adjacent channels decreasing as the adjacent channels travel from their respective distal end points to their respective proximal end points, the spacing changing from the distal to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points, the second plurality of channels being arranged such that adjacent channels of the second plurality of channels cooperate with a plurality of channels of the first plurality of channels to define a plurality of protrusions extending upwardly from the channels, a spacing between adjacent channels decreasing as the adjacent channels travel from their respective distal end points to their respective proximal end points, the spacing changing from the distal to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points, a second embossing pattern extending from the second end region towards the center region, the second embossing pattern including a third plurality of arcuate channels and a fourth plurality of arcuate channels, each one of the channels having a distal end point and a proximal end point, each one of the third plurality of arcuate channels shaped such that the channel arcs in a clockwise direction from its distal end point to its proximal end point, and each one of the fourth plurality of channels shaped such that the channel arcs in a counter-clockwise direction from its distal end point to its proximal end point, each one of the channels of the third plurality of channels being arranged such that it intersects a plurality of channels of the fourth plurality of channels and each one of the channels of the fourth plurality of channels being arranged such that it intersects a plurality of channels of the third plurality of channels, the third plurality of channels being arranged such that adjacent channels of the third plurality of channels cooperate with a plurality of channels of the fourth plurality of channels to define a plurality of protrusions extending upwardly from the channels, a spacing between adjacent channels decreasing as the adjacent channels travel from their respective distal end points to their respective proximal end points, the spacing changing from the distal to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points, the fourth plurality of channels being arranged such that adjacent channels of the fourth plurality of channels cooperate with a plurality of channels of the third plurality of channels to define a plurality of protrusions extending upwardly from the channels, a spacing between adjacent channels decreasing as the adjacent channels travel from their respective distal end points to their respective proximal end points, the spacing changing from the distal to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points, wherein the second embossing pattern is a mirror image of the first embossing pattern, a third embossing pattern located in the central region, the third embossing pattern including a plurality of channels extending radially outward from a intersection of the longitudinally extending centerline and the transversely extending centerline, the channels of the third embossing pattern cooperating to define a plurality of protrusions extending radially outward from the intersection, and the channels of the third embossing pattern cooperating to define a central protrusion, the central protrusion having a center located at the intersection of the longitudinally extending centerline and the transversely extending centerline, each of the first and second plurality of channels having a width in the range of between about 0.5 mm to about 5 mm and a depth in the range of about 0.5 mm to about 3 mm, each of the third and fourth plurality of channels having a width in the range of between about 0.5 mm to about 5 mm and a depth in the range of 0.5 mm to about 3 mm, each of the channels of the third embossing pattern having a width in the range of between about 0.5 mm to about 5 mm and a depth in the range of 0.5 mm to about 3 mm, an outer embossing ring surrounding each of the first, second and third embossing patterns, the outer embossing ring being spaced inwardly relative to the first and second longitudinally extending edges and the first and second transversely extending edges of the core by a distance in the range of about 3 mm to about 20 mm, each of the distal end points of the first, second, third and fourth plurality of channels intersecting the outer embossing ring, the outer embossing ring having a width in the range of between about 0.5 and about 5 mm and a depth in the range of between about 0.5 mm and 3 mm.

BRIEF DESCRIPTION OF THE DRAWINGS

Examples of embodiments of the present invention will now be described with reference to the drawings, in which.

DETAILED DESCRIPTION OF THE INVENTION

The present invention generally relates to disposable absorbent articles such as sanitary napkins, pantiliners, absorbent products for incontinence, and other disposable absorbent articles worn close to a wearer's body. As used herein, the term "sanitary napkin" refers to an article which is worn by females in an undergarment adjacent to the pudendal region and which is intended to absorb and contain various exudates which are discharged from the body (e.g., blood, menses, urine, and the like) and which is intended to be discarded after a single use (i.e., it is not intended to be laundered or otherwise restored or reused). Pantiliners are generally similar to sanitary napkins, except that they typically have lower capacity for absorbing fluids and are generally used to control non-menstrual discharges. Both sanitary napkins and pantiliners are typically attached or secured to a users undergarment and positioned between the undergarment and wearer's pudendal region. Adult incontinence articles, diapers, and interlabial devices are yet other disposable absorbent articles designed to manage various bodily exudates and may benefit from the embodiments of the invention described herein.

Absorbent articles according to the present invention provide superior fluid handling characteristics, and more specifically are particularly adept at providing enhanced wicking characteristics in the longitudinal direction of the absorbent article. Specifically, absorbent articles according to the present invention include an embossing pattern that provides enhanced fluid wicking in the longitudinal direction of the absorbent article thereby enabling the absorbent article to effectively utilize its total fluid handling capacity.

As used herein the "distal end point" of a channel is that portion of the channel located the furthest from the center of the sanitary napkin and the "proximal end point" is that portion of the channel of the napkin located closest to the center of the sanitary napkin.

Figure 1:
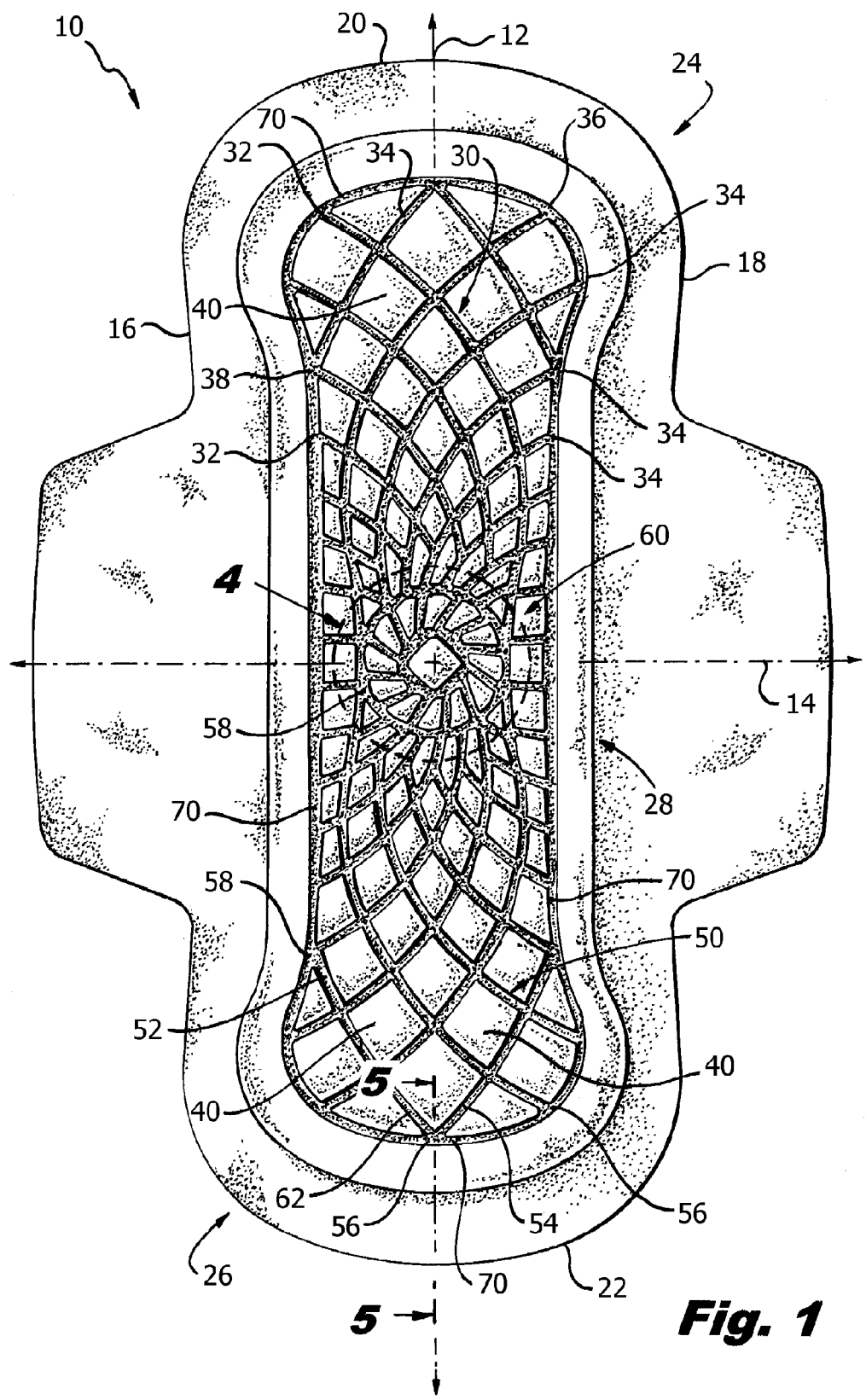
FIG. 1 is a top plan view of a sanitary napkin in accordance with an embodiment of the present invention.

A specific embodiment of the sanitary napkin 10 according to the present invention is illustrated in FIG. 1. The sanitary napkin 10 includes a first a longitudinally extending centerline 12, a transversely extending centerline 14, a first longitudinal edge 16, a second longitudinal edge 18, a first transverse edge 20, a second transverse edge 22, a first end region 24, a second end region 26, and a central region 28 located between the first end second end regions, 24 and 26.

The napkin 10 further includes a first embossing pattern 30 extending from the first end region 24 towards the center region 28. The first embossing pattern includes a first plurality of arcuate channels 32 and a second plurality of arcuate channels 34, each one of the channels 32 and 34 having a distal end point 36 and a proximal end point 38.

Each one of the first plurality of arcuate channels 32 is shaped such that the channel 32 arcs in a clockwise direction from its distal end point 36 to its proximal end point 38, and each one of the second plurality of channels 34 is shaped such that the channel arcs in a counter-clockwise direction from its distal end point 36 to its proximal end point 38.

Each one of the channels of the first plurality of channels 32 is arranged such that it intersects a plurality of channels 34 of the second plurality of channels 34 and each one of the channels 34 of the second plurality of channels 34 is arranged such that it intersects a plurality of channels 32 of the first plurality of channels 32.

The first plurality of channels 32 is arranged such that adjacent channels 32 of the first plurality of channels 32 cooperate with a plurality of channels 34 of the second plurality of channels 34 to define a plurality of protrusions 40 extending upwardly from the channels 32.

As seen in FIG. 1, a spacing between adjacent channels 32 decreases as the adjacent channels 32 travel from their respective distal end points 36 to their respective proximal end points 38 The spacing changes between adjacent channels 32 at a rate of between about 0.1 mm to about 1 mm per 1 millimeter length of distance traveled along the path of the channel 32. Due to the converging nature of the channels 32 a size of each of the protrusions 40 defined between adjacent channels 32 decreases as the adjacent channels 32 travel from their respective distal end points 36 to their respective proximal end points 38.

Each of the second plurality of channels 34 is arranged such that adjacent channels 34 of the second plurality of channels 34 cooperate with a plurality of channels 32 of the first plurality of channels 32 to define the plurality of protrusions 40 extending upwardly from the channels 34. Likewise a spacing between adjacent channels 34 decreases as the adjacent channels 34 travel from their respective distal end points 36 to their respective proximal end points 38. The spacing changes between adjacent channels 34 at a rate of between about 0.1 mm to about 1 mm per 1 millimeter length of distance traveled along the path of the channel 34. Due to the converging nature of the channels 34 a size of each of the protrusions 40 defined between adjacent channels 34 decreases as the adjacent channels 34 travel from their respective distal end points 36 to their respective proximal end points 38.

The sanitary napkin 10, further includes a second embossing pattern 50 extending from the second end region 26 towards the center region 28. The second embossing pattern 50 includes a third plurality of arcuate channels 52 and a fourth plurality of arcuate channels 54. Each one of the channels 52 and 54 has a distal end point 56 and a proximal end point 58.

Each one of the third plurality of arcuate channels 52 is shaped such that the channel 52 arcs in a clockwise direction from its distal end point 56 to its proximal end point 58. Each one of the fourth plurality of channels 54 shaped such that the channel 54 arcs in a counter-clockwise direction from its distal end point 56 to its proximal end point 58.

Each one of the channels 52 of the third plurality of channels 52 is arranged such that it intersects a plurality of channels 54 of the fourth plurality of channels 54 and each one of the channels 54 of the fourth plurality of channels 54 is arranged such that it intersects a plurality of channels 52 of the third plurality of channels 52.

The third plurality of channels 52 are arranged such that adjacent channels 52 of the third plurality of channels 52 cooperate with a plurality of channels 54 of the fourth plurality of channels 54 to define a plurality of protrusions 40 extending upwardly from the channels.

As seen in FIG. 1, a spacing between adjacent channels 52 decreasing as the adjacent channels 52 travel from their respective distal end points 56 to their respective proximal end points 58. The spacing changes between adjacent channels 52 at a rate of between about 0.1 mm to about 1 mm per 1 millimeter length of distance traveled along the path of the channel 52. Due to the converging nature of the channels 52 a size of each of the protrusions 40 defined between adjacent channels 52 decreases as the adjacent channels 52 travel from their respective distal end points 56 to their respective proximal end points 58. Due to the converging nature of the channels 52, a size of each of the protrusions 40 defined between adjacent channels 52 decreases as the adjacent channels 52 travel from their respective distal end points 56 to their respective proximal end points 58.

The fourth plurality of channels 54 are arranged such that adjacent channels 54 of the fourth plurality of channels 54 cooperate with a plurality of channels 52 of the third plurality of channels 52 to define a plurality of protrusions 40 extending upwardly from the channels 54. A spacing between adjacent channels 54 decreases as the adjacent channels 54 travel from their respective distal end points 56 to their respective proximal end points 58. The spacing changes between adjacent channels 54 at a rate of between about 0.1 mm to about 1 mm per 1 millimeter length of distance traveled along the path of the channel 54. In one embodiment of the invention, the second embossing pattern 50 is a mirror image of the first embossing pattern 30.

Figure 4:
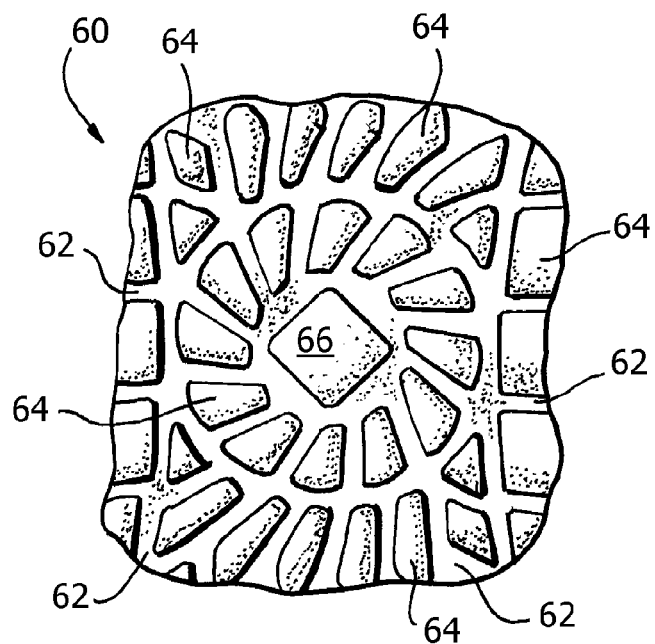
FIG. 4 is an enlarged detail view of the portion of the napkin encircled by circle 4 in FIG. 1.
Figure 5:
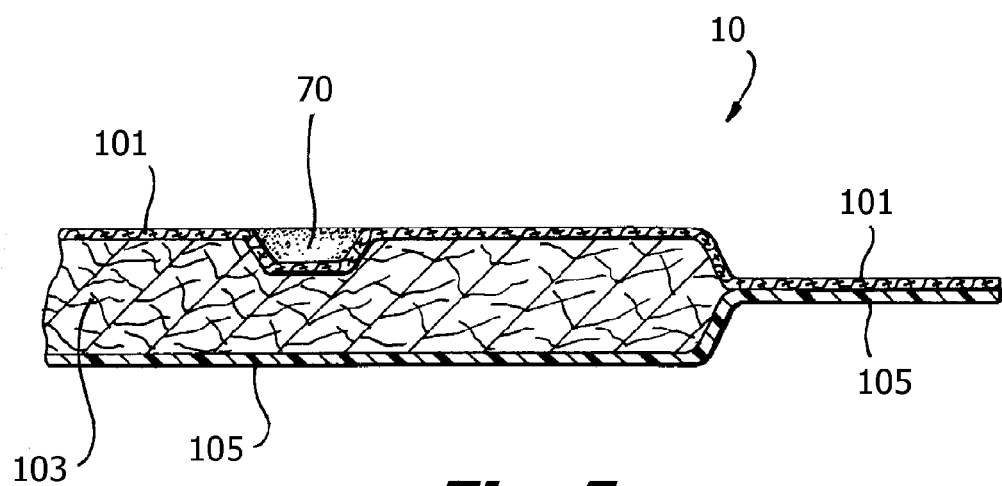
FIG. 5 is a cross sectional view taken along line 5-5 of the sanitary napkin shown in FIG. 1.

As best seen in FIG. 1 and 4, the sanitary napkin further includes a third embossing pattern 60 located in the central region 28. The third embossing pattern 60 includes a plurality of channels 62 extending radially outward from a intersection of the longitudinally extending centerline 12 and the transversely extending centerline 14. The channels 62 of the third embossing pattern 60 cooperate to define a plurality of protrusions 64 extending radially outward from the intersection. The channels 62 of the third embossing pattern 60 also cooperate to define a central protrusion 66, the central protrusion 66 has a center located at the intersection of the longitudinally extending centerline 12 and the transversely extending centerline 14.

In one embodiment of the invention, each of the first 32, second 34, third 52 and fourth 54 plurality of channels have a width in the range of between about 0.5 mm to about 5 mm and a depth in the range of 0.5 mm to about 3 mm. In one embodiment of the invention, each of the channels 62 of the third embossing pattern 60 has a width in the range of between about 0.5 mm and about 5 mm, and a depth in the range of 0.5 mm to about 3 mm.

The sanitary napkin 10 further includes an outer embossing ring 70 surrounding each of the first 30, second 50 and third 60 embossing patterns. The outer embossing ring 70 is spaced inwardly relative to the first 117a and second 117a longitudinally extending edges and the first 119a and second 119a transversely extending edges of the core 10 by a distance in the range of about 3 mm to about 20 mm.

In one embodiment of the invention, the outer embossing ring 70 is arranged such that each of the distal ends points 38 and 58 of the first 32, second 34, third 52 and fourth 54 plurality of channels intersect the outer embossing ring 70. In one embodiment of the invention, the outer embossing ring 70 has a width in the range of between about 0.5 mm and about 5 mm, and a depth in the range of 0.5 mm to about 3 mm.

Preferably the channels 32, 34, 52, 54, and 62 of first 30, second 50 and third 60 embossing patterns, as well as the outer embossing ring 70, are interconnected so as to form a network of continuously interconnected channels.

Figure 3:
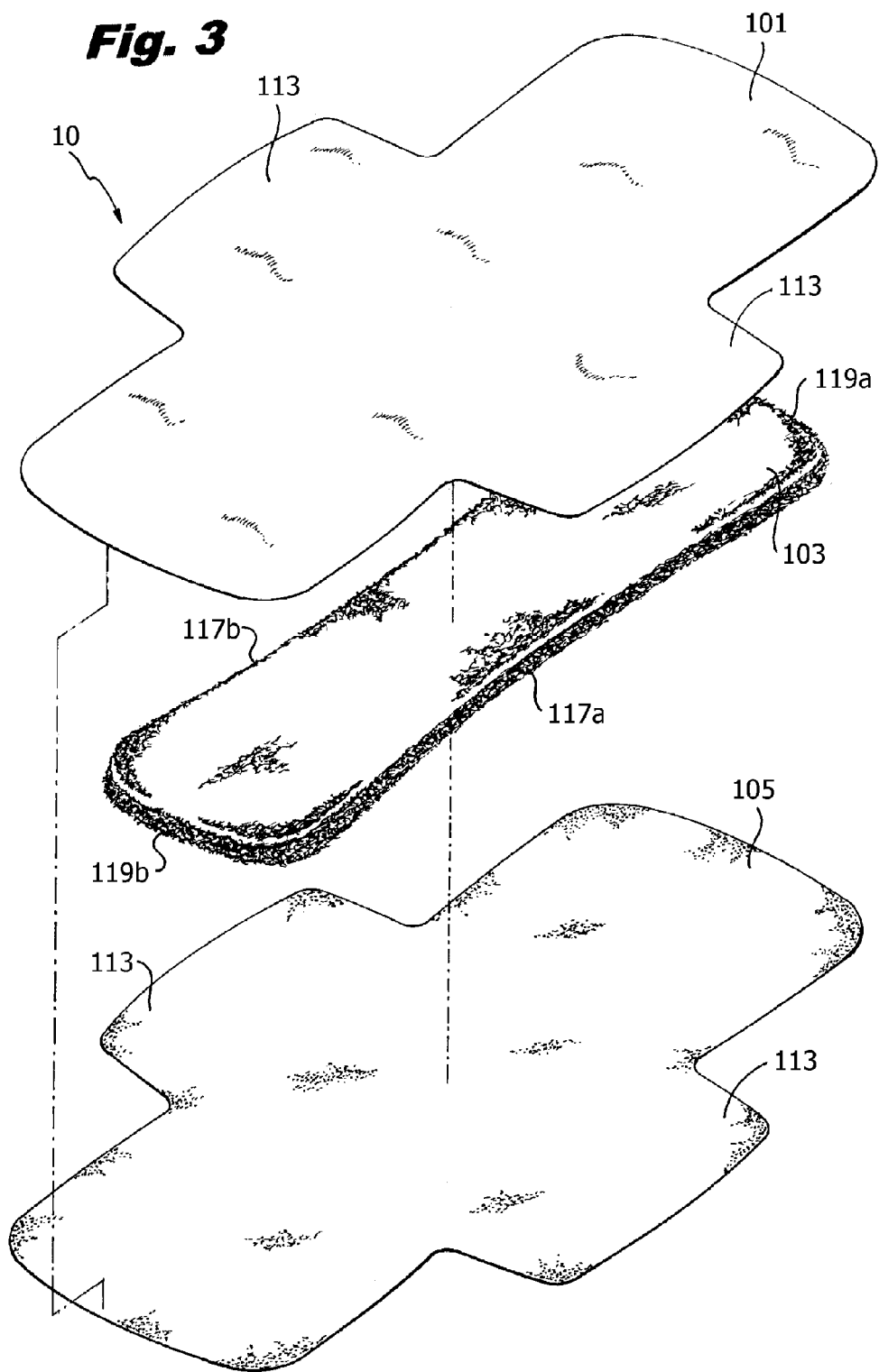
FIG. 3 is a exploded perspective view of the napkin shown in FIG. 1 depicting the cover layer, barrier layer and absorbent core thereof.

Referring to FIG. 3, the sanitary napkin 10 comprises a fluid-permeable cover layer 101, a liquid-impervious barrier layer 105 and an absorbent core 103 intermediate the fluid-permeable cover layer 101 and the liquid-impervious barrier layer 105. The cover layer 101 has a top surface that forms the body facing surface 81 of the sanitary napkin 10. The cover layer 101 is liquid permeable, and generally compliant, soft feeling, and non-irritating to the user's skin. It can be made from any of the materials conventional for this type of use. The cover layer 101 generally functions to transport fluid away from the wearer into the sanitary napkin 10. In this manner, fluid and moisture are removed from contacting the wearer, thus making the wearer feel dry and comfortable. Non-limiting examples of suitable materials that can be used as the cover layer 101 are woven and nonwoven fabrics formed from polyester, polypropylene, nylon, and/or rayon fibers or the topsheet may be an apertured thermo-plastic film and formed films. The cover layer 101 may optionally be treated with surfactant to manipulate the hydrophobicity/hydrophilicty thereof to facilitate optimal fluid transport properties. The fibers or other materials which make up the cover layer 101 should not collapse or lose their resiliency when subjected to body fluid. The cover layer 101 may be formed from, for example, staple fibers of polypropylene or other suitable materials. The fibers may be oriented by a carding process and thermally bonded via embossing. The basis weight of the cover layer 101 may range from about 10 grams per square meter (gsm) to about 40 gsm.

Figure 2:
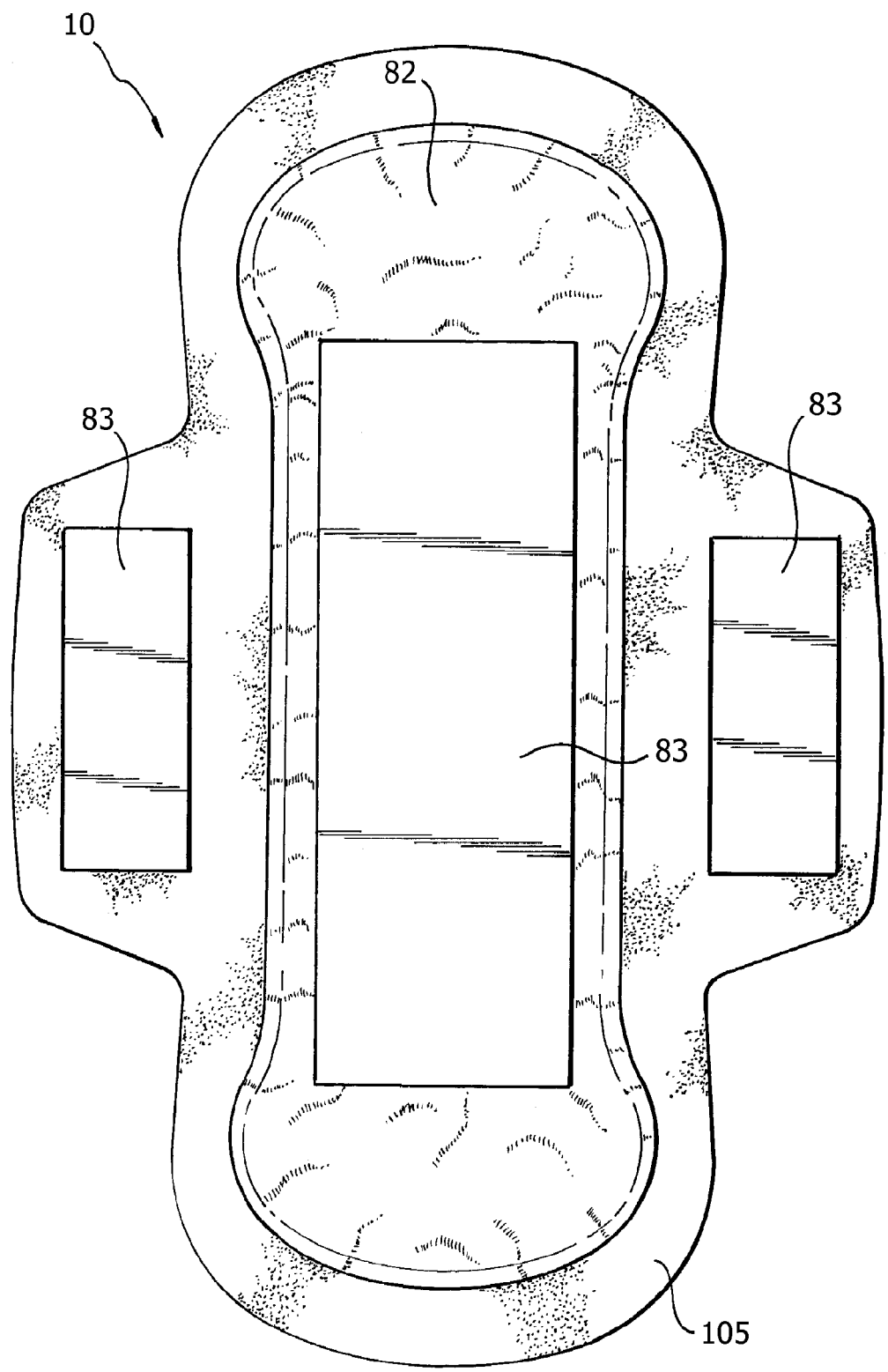
FIG. 2 is a bottom plan view of the sanitary napkin shown in FIG. 1.

The barrier 105 has a bottom surface that forms the garment facing surface 82 of the napkin 10. The barrier layer 105 is impervious to liquids and, thus, prevents bodily fluid that may be present at the interface between the absorbent core 103 and the barrier layer 105 from soiling the clothing of the user. Suitable materials that may be incorporated into the barrier layer 105 include, for example, embossed or non-embossed polyethylene films, microporous films, and laminated tissue, among other materials. The garment facing surface 82 of the barrier layer 105 is preferably provided with garment attachment adhesive for securing the napkin 10 to an undergarment during use. The garment attachment adhesive is preferably covered with removable release paper 83 to protect the garment attachment adhesive prior to use as seen in FIG. 2.

The absorbent core 103 provides the means for absorbing bodily fluid. Bodily fluid moving inward or "down" from the cover layer 101 is conveyed to the absorbent core 103 which retains the bulk of the fluid until the sanitary napkin 10 is discarded. The absorbent core 103 has a high capacity for absorbing liquids and may be capable of maintaining the definition of the plurality of protrusions and the plurality of channels described above during the wearing of the sanitary napkin 10. As shown in FIG. 3, the absorbent core includes first and second longitudinally extending edges 117a and 117b and first and second transversely extending edges 119a and 119b.

Examples of material that may be used in the construction of the absorbent core 103 include, for example, cellulosic fibers (preferably wood pulp, but cotton, flax and peat moss are acceptable), synthetic fibers, superabsorbent polymers (SAP) or superabsorbent fibers, as well organic binders and other materials known to the art of manufacturing absorbent core materials. The relative proportion of these materials may be varied to achieve sufficient absorbency, compressibility, and processibility. In one non-limiting example, the absorbent core 103 comprises from about 40 weight percent to about 95 weight percent cellulosic fibers, and from about 5 weight percent to about 60 weight percent superabsorbent polymer.

The absorbent core 103 may include any superabsorbent polymer (SAP). For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and other material known to the art of absorbent article manufacture.

The sanitary napkin 10 may optionally further include a transfer layer (not shown) and, if present, the transfer layer generally positioned directly underneath the cover layer 101, and the transfer layer directly contacts the absorbent core. The transfer layer provides the means of receiving body fluid from the fluid-pervious cover layer 101 and holding it until the absorbent core has an opportunity to absorb it. The transfer layer is, preferably, more dense than the fluid-pervious cover layer 101 and has a larger proportion of smaller pores than does the latter. These attributes allow the transfer layer to contain body fluid and hold it away from the outer side of the fluid-pervious cover layer 101, thereby preventing the fluid from re-wetting the fluid-pervious cover layer 101 and its surface. However, the transfer layer is preferably not so dense as to prevent the passage of the fluid through the transfer layer and into the underlying absorbent core.

The optional transfer layer may comprise various materials, including, for example, cellulose fibers such as from wood pulp, single component or bicomponent fibers that include thermoplastic materials (such as polyester, polypropylene, polyethylene, among others) in fiber or other forms, rayon, organic binders (such as copolymers of vinyl, acrylic and/or other monomers that may be coated onto thermoplastic fibers or otherwise incorporated into the transfer layer) among other materials known to the art. The transfer layer may, for example, have a basis weight in a range from about 20 grams per square meter (gsm) to about 120 gsm.

While the various material layers (cover, absorbent system, barrier) are described as separate layers, it is within the scope of the invention that one or more of these layers may be formed or integrated together and may actually not be discrete material layers, but rather a unitary layer possessing multiple functional properties.

Preferably the channels 32, 34, 52, 54, and 62 of first 30, second 50 and third 60 embossing patterns, as well as the outer embossing ring 70, extend into additional material layers of the sanitary napkin 10. For example, the channels 32, 34, 52, 54, and outer embossing ring 70 may be formed through the cover layer 101 and the absorbent core 103. By "formed through," the absorbent core 103, it is meant that if one were to follow a top surface absorbent core 103, one would find channels 32, 34, 52, 54, and an outer embossing ring 70 that correspond, register, with or align with the channels 32, 34, 52, 54, and outer embossing ring 70 of the cover layer 101. As such, the cover layer 101 follows the contours in the top surface of the absorbent core 103 with no appreciable macroscopic voids present between the two layers.

Referring again to FIG. 3, the absorbent core 103 may be confined to a laterally central region of the sanitary napkin 10 such that the cover layer 101 and barrier 105 extend beyond the peripheral edge of the absorbent core 103. Alternatively, the absorbent core 103 may extend laterally into the flap regions 113. The cover layer 101 and the barrier layer 105 are joined around the entire periphery of the sanitary napkin 10. The cover layer 101 and the barrier layer 105 can be joined by any means commonly used in the art for this purpose such as by gluing, crimping, or heat-sealing. Additional securement of the layers 101, 105 and 103 may be achieved by laminating one or more of these layers together.

The sanitary napkin 10 may be made using various conventional processes known to those of skill in the art, such as, for example, an embossing process in which one or more material layers of the sanitary napkin 10 are subject to mechanical and thermal energy to form the channels 32, 34, 52, 54, and 62 of first 30, second 50 and third 60 embossing patterns, as well as the outer embossing ring 70.

We claim:
1. A sanitary napkin comprising:
a cover layer;
a barrier layer;
an absorbent core arranged between the cover layer and the barrier layer, the absorbent core including first and second longitudinally extending edges and first and second transversely extending edges;
a longitudinally extending centerline;
a transversely extending centerline;
a first and second longitudinal edge;
a first and second transverse edge;
a first end region and a second end region,
a central region arranged between the first and second end regions;
a first embossing pattern extending from the first end region towards the center region, the first embossing pattern including a first plurality of arcuate channels and a second plurality of arcuate channels, each one of the channels having a distal end point and a proximal end point, each one of the first plurality of arcuate channels shaped such that the channel arcs in a clockwise direction from its distal end point to its proximal end point, and each one of the second plurality of channels shaped such that the channel arcs in a counter-clockwise direction from its distal end point to its proximal end point, each one of the channels of the first plurality of channels being arranged such that it intersects a plurality of channels of the second plurality of channels and each one of the channels of the second plurality of channels being arranged such that it intersects a plurality of channels of the first plurality of channels,
the first plurality of channels being arranged such that adjacent channels of the first plurality of channels cooperate with a plurality of channels of the second plurality of channels to define a plurality of protrusions extending upwardly from the channels, a spacing between adjacent channels decreasing as the adjacent channels travel from their respective distal end points to their respective proximal end points, the spacing changing from the distal to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points,
the second plurality of channels being arranged such that adjacent channels of the second plurality of channels cooperate with a plurality of channels of the first plurality of channels to define a plurality of protrusions extending upwardly from the channels, a spacing between adjacent channels decreasing as the adjacent channels travel from their respective distal end points to their respective proximal end points, the spacing changing from the distal to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points,
a second embossing pattern extending from the second end region towards the center region, the second embossing pattern including a third plurality of arcuate channels and a fourth plurality of arcuate channels, each one of the channels having a distal end point and a proximal end point, each one of the third plurality of arcuate channels shaped such that the channel arcs in a clockwise direction from its distal end point to its proximal end point, and each one of the fourth plurality of channels shaped such that the channel arcs in a counter-clockwise direction from its distal end point to its proximal end point, each one of the channels of the third plurality of channels being arranged such that it intersects a plurality of channels of the fourth plurality of channels and each one of the channels of the fourth plurality of channels being arranged such that it intersects a plurality of channels of the third plurality of channels,
the third plurality of channels being arranged such that adjacent channels of the third plurality of channels cooperate with a plurality of channels of the fourth plurality of channels to define a plurality of protrusions extending upwardly from the channels, a spacing between adjacent channels decreasing as the adjacent channels travel from their respective distal end points to their respective proximal end points, the spacing changing from the distal to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points,
the fourth plurality of channels being arranged such that adjacent channels of the fourth plurality of channels cooperate with a plurality of channels of the third plurality of channels to define a plurality of protrusions extending upwardly from the channels, a spacing between adjacent channels decreasing as the adjacent channels travel from their respective distal end points to their respective proximal end points, the spacing changing from the distal to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points,
wherein the second embossing pattern is a mirror image of the first embossing pattern,
a third embossing pattern located in the central region, the third embossing pattern including a plurality of channels extending radially outward from a intersection of the longitudinally extending centerline and the transversely extending centerline, the channels of the third embossing pattern cooperating to define a plurality of protrusions extending radially outward from the intersection, and the channels of the third embossing pattern cooperating to define a central protrusion, the central protrusion having a center located at the intersection of the longitudinally extending centerline and the transversely extending centerline, each of the first and second plurality of channels having a width in the range of between about 0.5 mm to about 5 mm and a depth in the range of about 0.5 mm to about 3 mm, each of the third and fourth plurality of channels having a width in the range of between about 0.5 mm to about 5 mm and a depth in the range of about 0.5 mm to about 3 mm, each of the channels of the third embossing pattern having a width in the range of between about 0.5 mm to about 5 mm and a depth in the range of about 0.5 mm to about 3 mm, an outer embossing ring surrounding each of the first, second and third embossing patterns, the outer embossing ring being spaced inwardly relative to the first and second longitudinally extending edges and the first and second transversely extending edges of the core by a distance in the range of about 3 mm to about 20 mm, each of the distal end points of the first, second, third and fourth plurality of channels intersecting the outer embossing ring, the outer embossing ring having a width in the range of between about 0.5 mm and 5 mm and a depth in the range of between 0.5 mm and 3 mm.

2. A sanitary napkin comprising:

a cover layer;

a barrier layer;

an absorbent core arranged between the cover layer and the barrier layer, the absorbent core including first and second longitudinally extending edges and first and second transversely extending edges;

a longitudinally extending centerline;

a transversely extending centerline;

a first and second longitudinal edge;

a first and second transverse edge;

a first end region and a second end region, a central region arranged between the first and second end regions;

a first embossing pattern extending from the first end region towards the center region, the first embossing pattern including a first plurality of arcuate channels and a second plurality of arcuate channels, each one of the channels having a distal end point and a proximal end point, each one of the first plurality of arcuate channels shaped such that the channel arcs in a clockwise direction from its distal end point to its proximal end point, and each one of the second plurality of channels shaped such that the channel arcs in a counter-clockwise direction from its distal end point to its proximal end point, each one of the channels of the first plurality of channels being arranged such that it intersects a plurality of channels of the second plurality of channels and each one of the channels of the second plurality of channels being arranged such that it intersects a plurality of channels of the first plurality of channels, the first plurality of channels being arranged such that adjacent channels of the first plurality of channels cooperate with a plurality of channels of the second plurality of channels to define a plurality of protrusions extending upwardly from the channels, a spacing between adjacent channels decreasing as the adjacent channels travel from their respective distal end points to their respective proximal end points, the spacing changing from the distal end points to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points, the second plurality of channels being arranged such that adjacent channels of the second plurality of channels cooperate with a plurality of channels of the first plurality of channels to define a plurality of protrusions extending upwardly from the channels, a spacing between adjacent channels decreasing as the adjacent channels travel from their respective distal end points to their respective proximal end points, the spacing changing from the distal end points to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points, a second embossing pattern extending from the second end region towards the center region, the second embossing pattern including a third plurality of arcuate channels and a fourth plurality of arcuate channels, each one of the channels having a distal end point and a proximal end point, each one of the third plurality of arcuate channels shaped such that the channel arcs in a clockwise direction from its distal end point to its proximal end point, and each one of the fourth plurality of channels shaped such that the channel arcs in a counter-clockwise direction from its distal end point to its proximal end point, each one of the channels of the third plurality of channels being arranged such that it intersects a plurality of channels of the fourth plurality of channels and each one of the channels of the fourth plurality of channels being arranged such that it intersects a plurality of channels of the third plurality of channels, the third plurality of channels being arranged such that adjacent channels of the third plurality of channels cooperate with a plurality of channels of the fourth plurality of channels to define a plurality of protrusions extending upwardly from the channels, a spacing between adjacent channels decreasing as the adjacent channels travel from their respective distal end points to their respective proximal end points, the spacing changing from the distal end points to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points, the fourth plurality of channels being arranged such that adjacent channels of the fourth plurality of channels cooperate with a plurality of channels of the third plurality of channels to define a plurality of protrusions extending upwardly from the channels, a spacing between adjacent channels decreasing as the adjacent channels travel from their respective distal end points to their respective proximal end points, the spacing changing from the distal end points to proximal end points at a rate of between about 0.1 mm to about 1 mm per 1 millimeter length of distance traveled along the path of the channel, a size of each of the protrusions defined between adjacent channels decreasing as the adjacent channels travel from their respective distal end points to their respective proximal end points, wherein the second embossing pattern is a mirror image of the first embossing pattern, a third embossing pattern located in the central region, the third embossing pattern including a plurality of channels extending radially outward from a intersection of the longitudinally extending centerline and the transversely extending centerline, the channels of the third embossing pattern cooperating to define a plurality of protrusions extending radially outward from the intersection, and the channels of the third embossing pattern cooperating to define a central protrusion, the central protrusion having a center located at the intersection of the longitudinally extending centerline and the transversely extending centerline, each of the first and second plurality of channels having a width in the range of between about 0.5 mm to about 5 mm and a depth in the range of about 0.5 mm to about 3 mm, each of the third and fourth plurality of channels having a width in the range of between about 0.5 mm to about 5 mm and a depth in the range of about 0.5 mm to about 3 mm, an outer embossing ring surrounding each of the first, second and third embossing patterns, the outer embossing ring being spaced inwardly relative to the first and second longitudinally extending edges and the first and second transversely extending edges of the core by a distance in the range of about 3 mm to about 20 mm.

3. The sanitary napkin according to claim 2, wherein each of the distal end points of the first, second, third and fourth plurality of channels intersect the outer embossing ring.

4. The sanitary napkin according to claim 2, wherein the outer embossing ring has a width in the range of between 0.5 mm and 5 mm and a depth in the range of between about 0.5 mm and 3 mm.

* * * * *